(12) United States Patent
Rasor

(10) Patent No.: US 9,063,116 B2
(45) Date of Patent: Jun. 23, 2015

(54) SYSTEM FOR MONITORING AND TREATING TRANSFORMER OIL

(71) Applicant: S.D. Myers, Inc., Tallmadge, OH (US)

(72) Inventor: Robert Rasor, Stow, OH (US)

(73) Assignee: S.D. Myers, Inc., Tallmadge, OH (US)

( * ) Notice: Subject to any disclaimer, the term of this patent is extended or adjusted under 35 U.S.C. 154(b) by 316 days.

(21) Appl. No.: 13/769,078

(22) Filed: Feb. 15, 2013

(65) Prior Publication Data

US 2014/0233605 A1  Aug. 21, 2014

(51) Int. Cl.
*G01K 13/00* (2006.01)
*G01N 33/28* (2006.01)

(52) U.S. Cl.
CPC .................. *G01N 33/2841* (2013.01)

(58) Field of Classification Search
USPC .................................. 374/152, 142
See application file for complete search history.

(56) References Cited

U.S. PATENT DOCUMENTS

| | | | |
|---|---|---|---|
| 2,323,524 A | 2/1941 | Downs, Jr. | |
| 3,398,208 A | 8/1968 | Ward | |
| 3,927,555 A | 12/1975 | Godwin et al. | |
| 3,998,738 A | 12/1976 | Kusay | |
| 4,019,977 A | 4/1977 | Hachadoorian et al. | |
| 4,437,082 A | 3/1984 | Walsh et al. | |
| 4,680,091 A | 7/1987 | Altmann et al. | |
| 5,403,475 A * | 4/1995 | Allen | 210/774 |
| 5,574,214 A | 11/1996 | Balton et al. | |
| 6,609,411 B1 | 8/2003 | Taylor et al. | |
| 8,282,832 B2 | 10/2012 | Cropp | |
| 2008/0099400 A1 | 5/2008 | Nemser et al. | |
| 2011/0267080 A1 | 11/2011 | Hedges | |
| 2012/0043505 A1* | 2/2012 | Bongardt | 252/394 |

OTHER PUBLICATIONS

Dry Keep Transformer Moisture Management System Descriptive Brochure, website: http://drykeepusa.tripod.com/system.html.
Piping and Instrumentation Diagram, SD Myers Engineering Services, 180 South Ave., Tallmadge, OH 44278, Aug. 8, 2011.
Valve List DryMax GT.

* cited by examiner

*Primary Examiner* — Mirellys Jagan
(74) *Attorney, Agent, or Firm* — Emerson Thomson Bennett, LLC; Roger D. Emerson; Sergey Vernyuk

(57) ABSTRACT

A system for monitoring and treating transformer oil within an on-line electric transformer may include an oil filtration system using a first filter medium that removes acids dissolved in the transformer oil and a second filter medium that removes moisture from the transformer oil. A control and monitoring system may include a hydrogen sensor, a moisture sensor and a control module that receives and displays information and may be used remotely and wirelessly to control the systems. A monitoring dashboard may be positioned remotely and wirelessly receive and display information.

20 Claims, 11 Drawing Sheets

Alarm & Alert Codes

Alarm codes trigger automatic internal emails and result from Pro-Serve of from calculated values within the EPdb

| Alarm/Alert Code | Alarm or Alert? | Alarm Text | Trigger for INTERNAL Auto-Email | Possible X for reading | Source | Notes | Character Count |
|---|---|---|---|---|---|---|---|
| Alarm 01 | Alarm | Unit Off | 1 reading | | Pro-Serve | Customer hits the STOP button | 8 |
| Alarm 02 | Alarm | High Pressure | 1 reading | | Pro-Serve | High pressure due to high viscosity of oil (temp) or final filter needs changed. | |
| Alarm 03 | Alarm | Transformer solenoid valve failure | | 3 | Pro-Serve | Indicator on valve body tied to an alarm | 13 |
| Alarm 04 | Alarm | Leak Detected | 1 reading | 1 | Pro-Serve | High float in drip pan. | 17 |
| Not an alarm/alert | | H2 base ppm level | N/A | 1 | Epdb | Set 3 weeks after installation- set as a high point of what was seen as it drifts in a band of readings. | |
| Alarm 05 | Alarm | H2 PPM ROC- Daily Limit Alarm | 1 reading | 1 | Epdb | The ROC X ppm per consecutive readings | 31 |
| Alarm 06 | Alert | H2 PPM ROC- Weekly Alert | Weekly Report | 3 | Epdb | The ROC y ppm per week | 27 |
| Alarm 07 | Alert | H2 PPM ROC- Monthly Alert | Weekly Report | 1 | Epdb | The ROC z ppm per month | 27 |
| Alarm 08 | Alert | H2 PPM ROC- 3 Month Alert | Weekly Report | 1 | Epdb | The ROC bb ppm per 3 months | 27 |
| Alarm 09 | Alert | H2 PPM ROC- 6 Month Alert | Weekly Report | 1 | Epdb | The ROC bb ppm per 6 months | 27 |
| Alarm 10 | Alert | Max H2 ppm level | Weekly Report | 1 | Epdb | IEEE limit for hydrogen | 16 |
| Alarm 11 | Alert | Missing Moisture ppm | Investigate-1 reading? | 1 | Pro-Serve | Indicate a malfunction of the moisture sensor | 20 |

FIG. 10

| Alarm/Alert Code | Alarm or Alert? | Alarm Text | Trigger for INTERNAL Auto-Email | Possible X for reading | Source | Notes | Character Count |
|---|---|---|---|---|---|---|---|
| Alarm 12 | Alert | Missing temperature | Investigate- 3 readings? | 3 | Pro-Serve | Indicate a malfunction of the moisture sensor | 19 |
| Alarm 13 | Alert | % Saturation- QU | Weekly report | 1 | Epdb | Set 3 weeks after installation- set as high point of what was seen | 17 |
| Alarm 14 | Alert | % Saturation- UN | Weekly report | 1 | Epdb | QN and UN based on voltage class- an alarm | 17 |
| Alarm 15 | Alarm | H2 monitor service alarm activated | Alarm Active >8 hours | 1 | Pro-Serve |  | 34 |
| Alarm 16 | Alarm | Communications have been disabled | 48 hours w/o comm. | 1 | Epdb | No cell service OR the power to the unit has been disconnected | 34 |

FIG. 11

SYSTEM FOR MONITORING AND TREATING TRANSFORMER OIL

I. BACKGROUND

A. Field of Invention

This invention generally relates to systems used to treat transformer oil and more specifically relates to a system that continuously monitors and treats transformer oil to slow the natural aging process of transformers.

B. Description of the Related Art

Electric transformers are devices that take electricity at one voltage and change or transform the electricity into another voltage. Typically, transformers include paper insulation and a tank filed with oil used for cooling. The life of such a transformer is based on the life of the paper insulation. Insulation aging and loss of life is caused by oxidation. Heat, moisture and oxygen oxidize the oil and create acid. The acid and other oxidation byproducts degrade the paper and cause it to weaken, loosing tensile strength. Traditional oil reclamation is an effective way to correct the acid, slow aging and thereby extend the life of the transformer. However, such traditional oil reclamation apparatuses and methods cannot restore lost life.

What is needed is a system that continuously monitors and treats transformer oil to slow the natural aging process of the paper insulation and thus slow the aging process of the corresponding transformer.

II. SUMMARY

According to one embodiment of this invention, a system for monitoring and treating transformer oil within an associated on-line electric transformer may comprise: (A) an oil filtration system comprising: (1) a first filter container comprising a first filter medium that removes acids dissolved in the transformer oil from the transformer oil; and, (2) a second filter container comprising a second filter medium that removes moisture from the transformer oil; (B) an oil movement system that moves the transformer oil from the associated on-line transformer, through the transformer oil filtration system, and back into the associated on-line transformer;

the oil movement system comprising a pump; (C) a housing located near the associated on-line electric transformer that houses the first and second filter containers and the pump; and, (D) a control and monitoring system that: (1) comprises a hydrogen sensor that: (a) is positioned within the housing; and, (b) senses the amount of hydrogen in the transformer oil; (2) comprises a moisture sensor that: (a) is positioned within the housing; (b) senses the amount of moisture in the transformer oil; and, (c) senses the temperature of the transformer oil; (3) comprises a control module that: (a) is mounted to the housing; and, (b) receives and displays information from the hydrogen and moisture sensors; (4) comprises a monitoring dashboard remote from the housing that wirelessly receives and displays information from the hydrogen and moisture sensors; (5) determines parts per million (PPM) of moisture in the transformer oil; (6) determines the temperature of the transformer oil; (7) determines saturation of moisture in the in the transformer oil; (8) sets off an alarm when at least one of the following conditions occurs: (1) the PPM of moisture in the transformer oil is determined to be above a predetermined value; (2) the temperature of the transformer oil is determined to be above a predetermined value; and, (3) the saturation of moisture in the in the transformer oil is determined to be above a predetermined value; and, (9) posts the information from the hydrogen and moisture sensors on an internet based data center.

According to another embodiment of this invention, a system for monitoring and treating transformer oil within an associated on-line electric transformer may comprise: (A) an oil filtration system comprising: (1) a first filter container comprising a first filter medium that removes acids dissolved in the transformer oil from the transformer oil; and, (2) a second filter container comprising a second filter medium that removes moisture from the transformer oil; (B) an oil movement system that moves the transformer oil from the associated on-line transformer, through the transformer oil filtration system, and back into the associated on-line transformer; (C) a housing located near the associated on-ling electric transformer that houses the first and second filter containers; and, (D) a control and monitoring system comprising: (1) a hydrogen sensor that senses the amount of hydrogen in the transformer oil; (2) a moisture sensor that senses the amount of moisture and the temperature of the transformer oil; (3) a control module juxtaposed to the housing that receives and displays information from the hydrogen and moisture sensors; and, (4) a monitoring dashboard remote from the housing that wirelessly receives and displays information from the hydrogen and moisture sensors.

According to yet another embodiment of this invention, a method of monitoring and treating transformer oil within an associated on-line electric transformer may comprise the steps of: (A) providing a system for monitoring and treating the transformer oil within the associated on-line electric transformer that comprises: (1) an oil filtration system comprising: (a) a first filter container comprising a first filter medium; and, (b) a second filter container comprising a second filter medium; (2) an oil movement system; (3) a housing that houses the first and second filter containers; and, (4) a control and monitoring system comprising: (a) a hydrogen sensor; (b) a moisture sensor; (c) a control module juxtaposed to the housing; and, (d) a monitoring dashboard remote from the housing; (B) locating the housing near the associated on-line electric transformer; (C) connecting the oil filtration system to the associated on-line electric transformer; (D) using the oil movement system to move the transformer oil from the associated on-line transformer and through the transformer oil filtration system; (E) removing acids dissolved in the transformer oil from the transformer oil as the transformer oil is moved through the first filter container; (F) removing moisture from the transformer oil as the transformer oil is moved through the second filter container; (G) using the hydrogen sensor to sense the amount of hydrogen in the transformer oil; (H) using the moisture sensor to sense the amount of moisture in the transformer oil; (I) using the control module to receive and display information from the hydrogen and moisture sensors; (J) using the monitoring dashboard to wirelessly receive and display information from the hydrogen and moisture sensors; and, (K) using the oil movement system to move the transformer oil back into the associated on-line transformer. Steps (A) through (K) may slow the natural aging process of the associated on-line electric transformer.

One advantage of this invention is that transformer oil can be monitored and treated continuously.

Another advantage of this invention is that transformer oil can be monitored and treated while the transformer remains on-line.

Still another advantage of this invention is that the unwanted oxidation process can be controlled greatly reducing the time and money required for maintenance.

Another advantage of this invention is that the transformer oil can be monitored and the invention can be controlled from a remote location.

Other benefits and advantages of this invention will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein:

FIG. 10 shows some embodiments of alert/alarm condition triggers.

FIG. 11 shows some other embodiments of alert/alarm condition triggers.

IV. DETAILED DESCRIPTION

Figure 1:
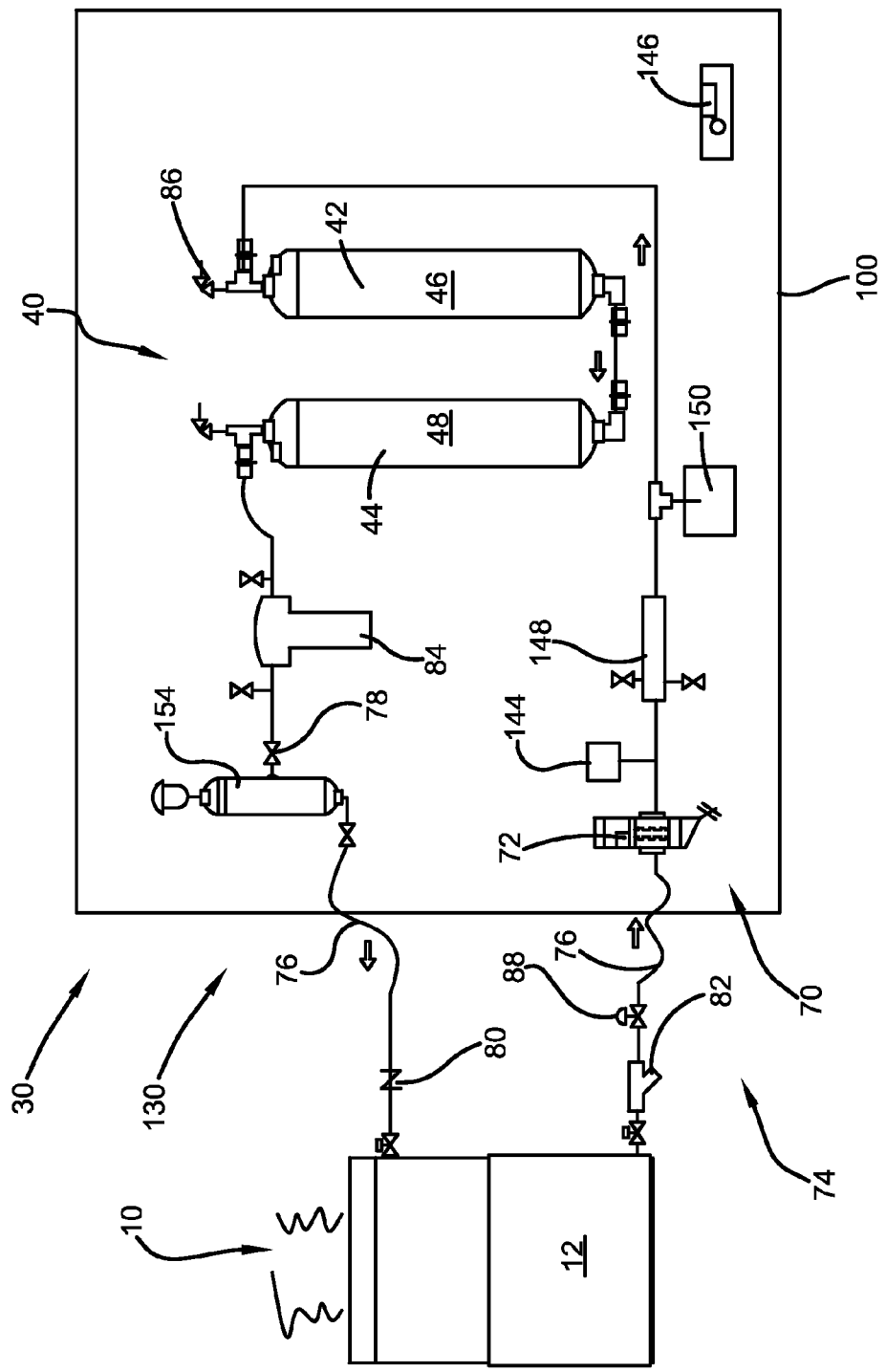
FIG. 1 is a schematic representation of an electric transformer and a system for monitoring and treating transformer oil.

Referring now to the drawings wherein the showings are for purposes of illustrating embodiments of the invention only and not for purposes of limiting the same, and wherein like reference numerals are understood to refer to like components, FIG. 1 shows a schematic of an electric transformer 10 and a system for monitoring and treating transformer oil 30 that may include embodiments of this invention. While this invention is particularly designed for use with electric transformers that include paper insulation, it will work with any type and size of electric transformer chosen with the sound judgment of a person of skill in the art that contains oil 12 needing to be treated. In one embodiment, the system for monitoring and treating transformer oil 30 is used with a transformer that is on-line. By on-line it is meant that the transformer is in normal operation. In another embodiment, the system for monitoring and treating transformer oil 30 may be used with a transformer that is off-line, that is, not in operation. The system for monitoring and treating transformer oil 30, may include four major systems/components: an oil filtration system 40, an oil movement system 70, a housing 100, and a control and monitoring system 130. These systems/components will now be described.

Figure 2:
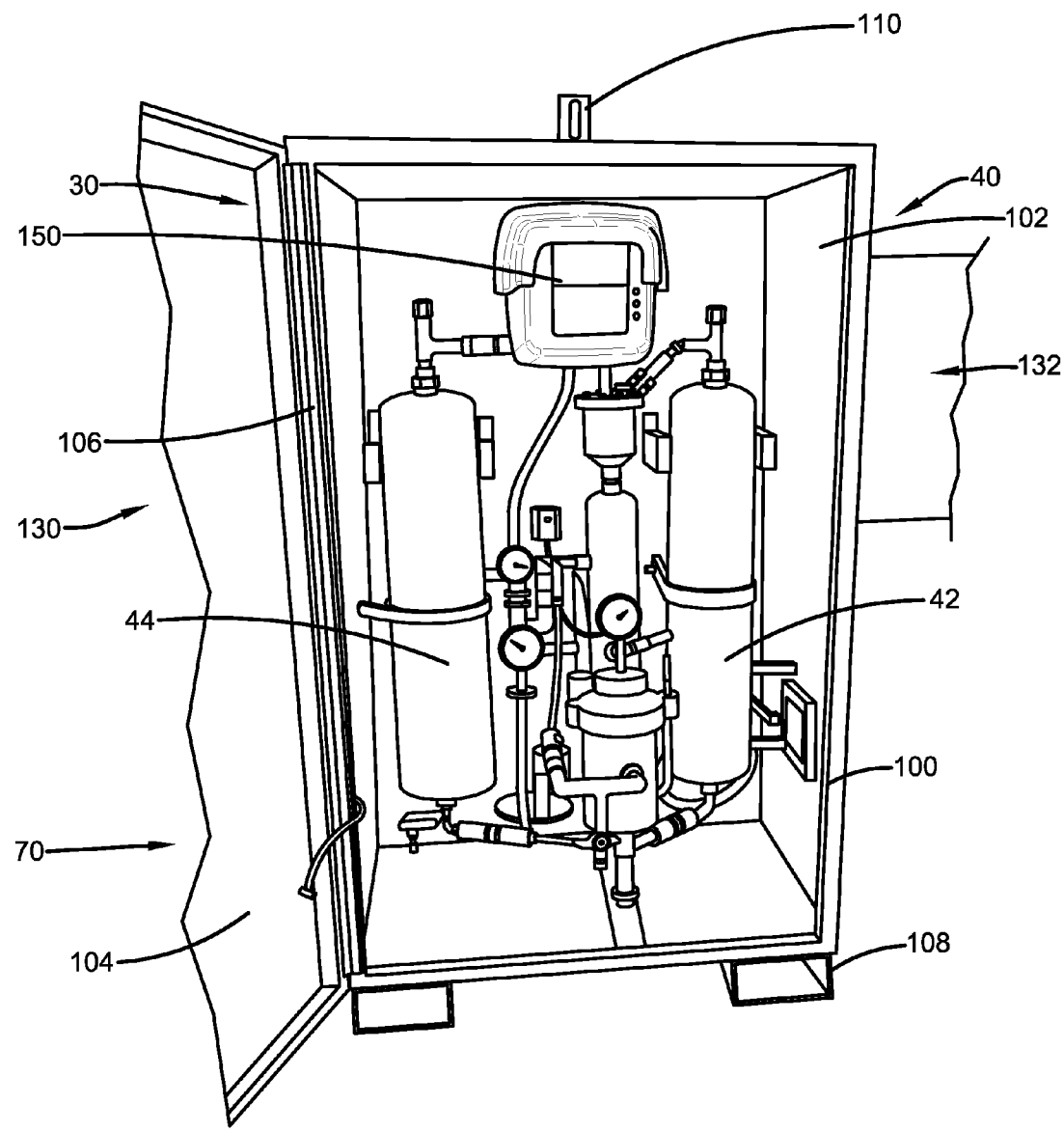
FIG. 2 is a front view of a system for monitoring and treating transformer oil with the door of the housing open.
Figure 3:
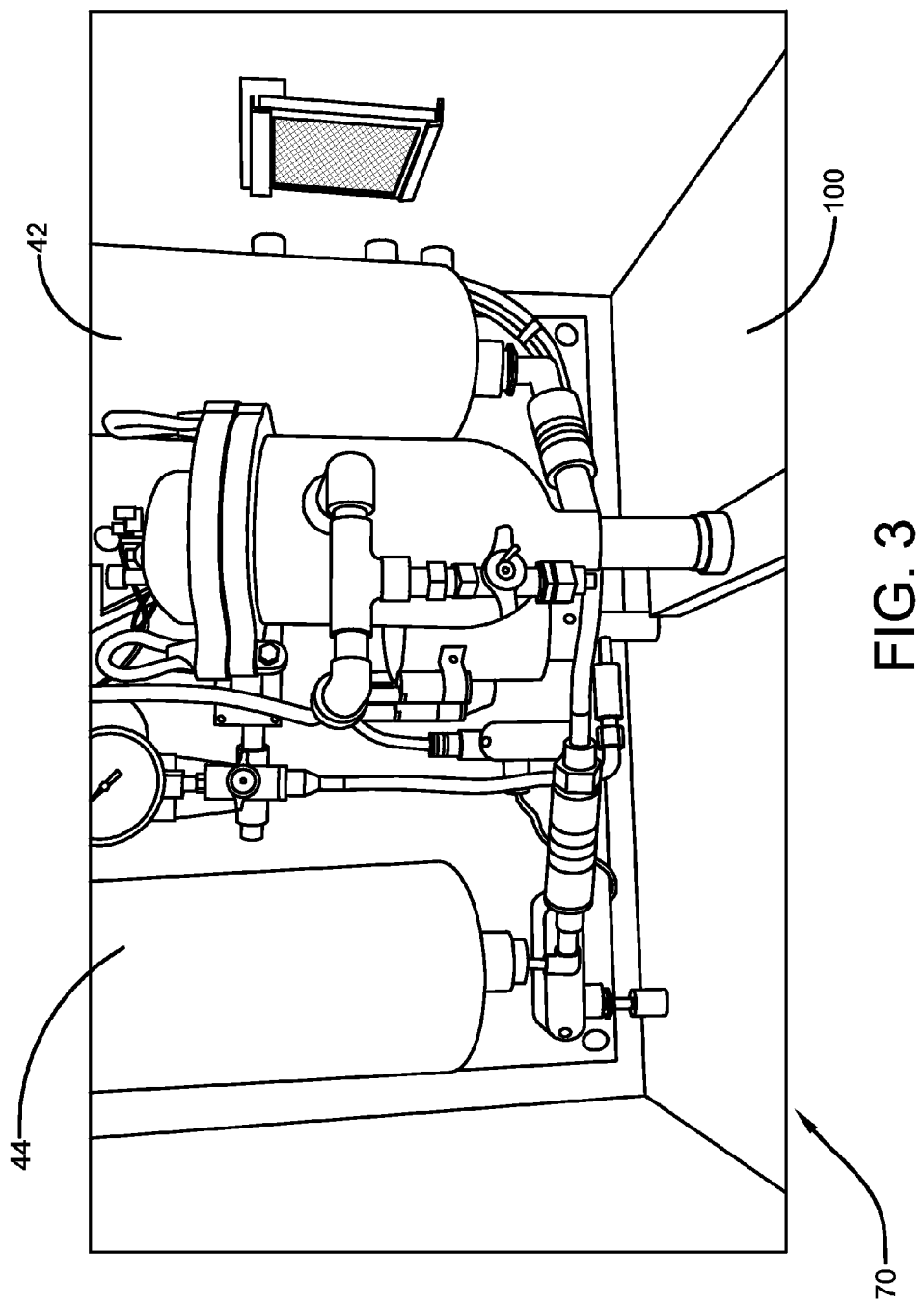
FIG. 3 is a close-up view of a portion of the system for monitoring and treating transformer oil shown in FIG. 2.

With reference to FIGS. 1-3, the oil filtration system 40 may be used to control oxidation by removing unwanted contaminates (particles that are not dissolved in the oil, including moisture or water) and unwanted solutes (substances that are dissolved in the oil, including acids). The oil filtration system 40 may include a first filter container 42 containing a first filter medium 46 and a second filter container 44 containing a second filter medium 48. In one embodiment, the first filter medium 46 removes acids dissolved in the transformer oil from the transformer oil. In a specific embodiment, the first filter medium 46 is primarily or exclusively a granular alumina. In one embodiment, the second filter medium 48 removes moisture (water) from the transformer oil. In one specific embodiment, the second filter medium 48 is primarily or exclusively alumina beads. It has been discovered that by moving the oil through the first filter container 42 (and thus through the first filter medium 46) before moving the oil through the second filter container 44 (and thus through the second filter medium 48), a better overall filtering performance is obtained. However, in another embodiment, the oil may be moved through the second filter medium 48 before moving the oil through the first filter medium 46. In one embodiment, the first and second filter media 46, 48 are recyclable. This eliminates the need for disposal of the first and second filter media 46, 48.

With reference now to FIGS. 1-2, the oil movement system 70 may be used to move the transformer oil from the transformer 10, through the oil filtration system 40, and then back into the transformer 10. While the oil movement system 70 can be of any type and size chosen with the sound judgment of a person of skill in the art, the system 70 shown includes a pump 72 and oil piping 74 used to interconnect the various components. While the pump can be of any size and type chosen with the sound judgment of a person of skill in the art, the pump 72 shown delivers a flow rate of between 0.5, to 2.0, gallons per minute. In one embodiment, the oil piping 74 comprises a pair of hoses 76, 76 that make connection of the system for monitoring and treating transformer oil 30 easy to connect to (and disconnect from) the transformer 10. The oil movement system 70 may also include various known components that make the assembly and use of the oil piping 74, as well as maintenance issues, easy to accomplish. These components may include, for example, one or more: manual valves 78, check valves 80, strainers 82, filters 84, pressure safety valves 86, solenoid valves 88, an air eliminator 154 and a manifold 148. As the use and operation of these components, along with their symbols shown in FIG. 1, are well known to those of skill in the art, further details will not be provided here.

With reference now to FIGS. 1-3, the housing or enclosure 100 may be used to house and/or support various components used with the system for monitoring and treating transformer oil 30. For the embodiment shown, the housing 100 has an interior 102 defined by a back wall, a right side wall, a left side wall, a bottom, a top and a door 104 which may be moveable with respect to the walls between open and closed positions. In the embodiment shown, the door 104 is pivotal with respect to the walls about hinge(s) 106. Feet 108 may be add to the bottom and used to support the system for monitoring and treating transformer oil 30 both during shipment and during use with the transformer. Components that make up the system for monitoring and treating transformer oil 30 may be positioned within the housing (thus they are "housed") in accordance with the sound judgment of a person of skill in the art. For the embodiment shown, the oil filtration system 40 is housed as is the pump 72 and other components that make up the oil movement system 70. Some components of the control and monitoring system 130 may also be housed as will be discussed further below. One advantage of the housing 100 is that it is relatively small and compact, yet provides easy access to the components it houses (or components supported to the housing 100). The interior 102 of the housing 100 shown has a height of about 4 feet, a width of about 3 feet and a depth of about 2 feet thus having a volume of about 24 cubic feet. While the housing 100 can be formed of any material chosen with the sound judgment of a person of skill in the art, in one embodiment the housing 100 is formed of stainless steel. For the embodiment shown, the total weight of the housing (including all the components shown) is about 400 pounds, the power requirement is 5 amperes at 110 volts ac (alternating current) single phase.

With reference now to FIGS. 2, 4-6, and 10-11, the control and monitoring system 130 may be used to control the system for monitoring and treating transformer oil 30 and/or monitor one or more characteristics of the oil and/or components making up the system 30. The embodiments shown may include a control module 132 that is local, that is juxtaposed to the transformer 10 and/or housing 100, which may also be viewed and controlled remotely, and a monitoring dashboard 134 that is remote from the transformer 10 and/or housing 100. Both the control module 132 and the monitoring dashboard 134 may be viewed remotely from the system. The control module 132 will have the same screens and can be used by operators to control and/or monitor various functions of the system. Thus, the control module 132 may receive and display and/or permit inputs regarding information used to control and monitor the system for monitoring and treating transformer oil 30. The monitoring dashboard 134 may be used for monitoring and treating transformer oil and viewing alarms/alerts. FIGS. 10 and 11 show embodiments of alert/alarm condition triggers that may be used.

Figure 4:
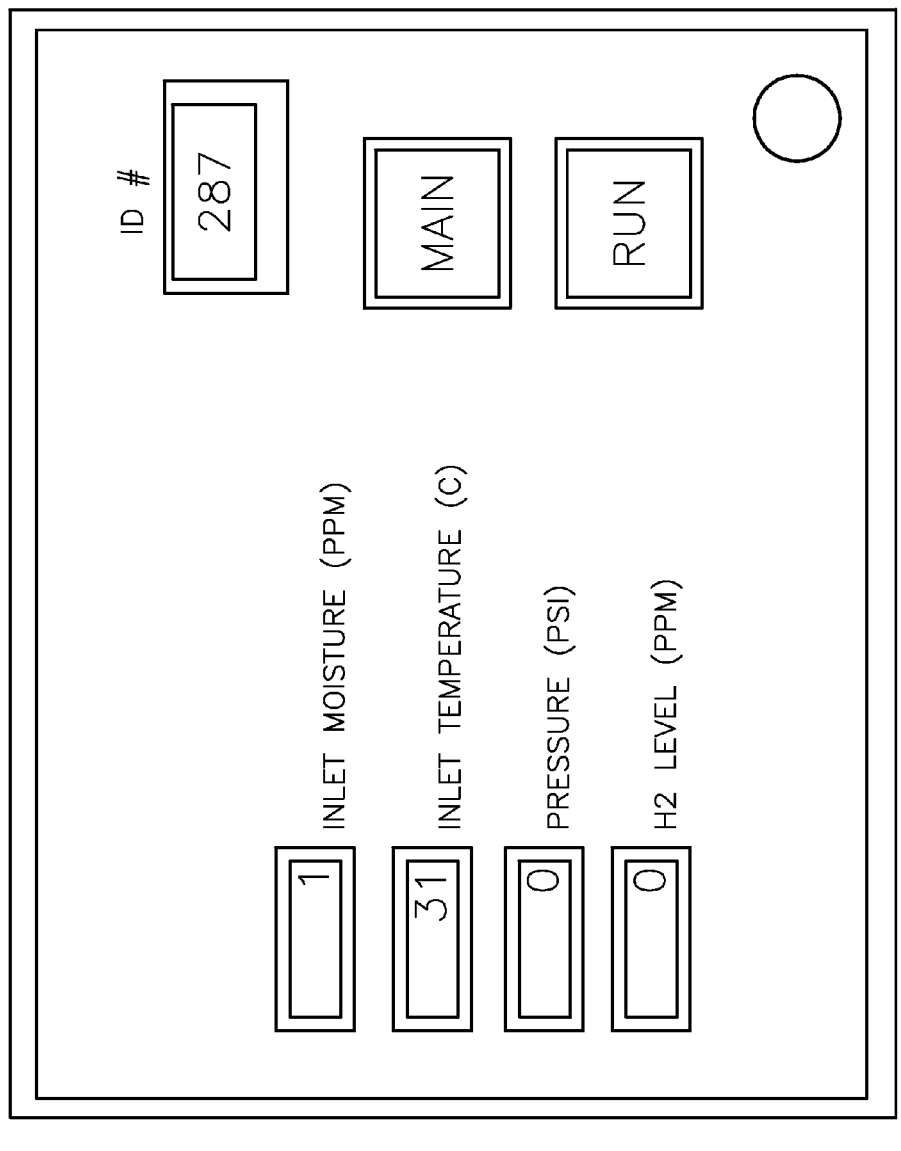
FIG. 4 is a view of other embodiments of a control module.
Figure 5:
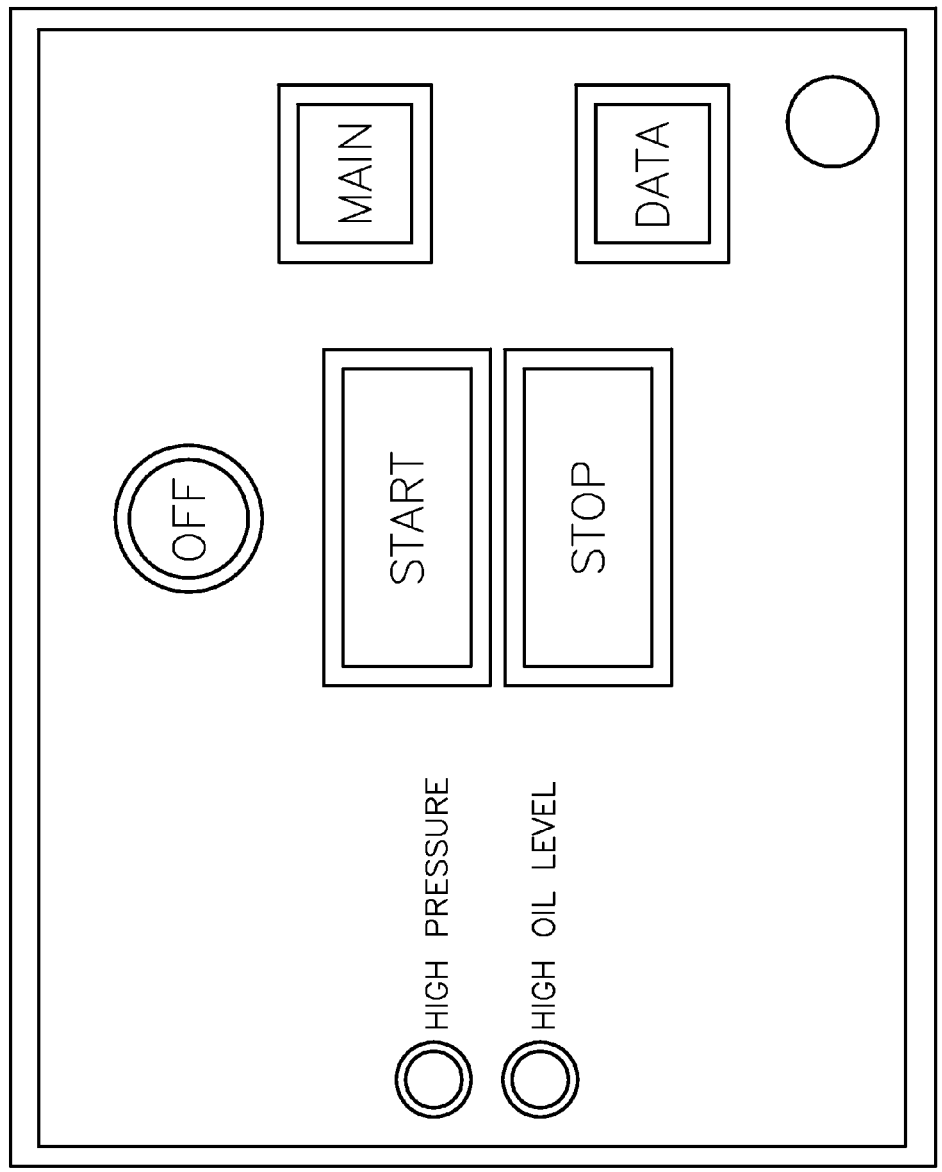
FIG. 5 is a view of yet other embodiments of a control module.
Figure 6:
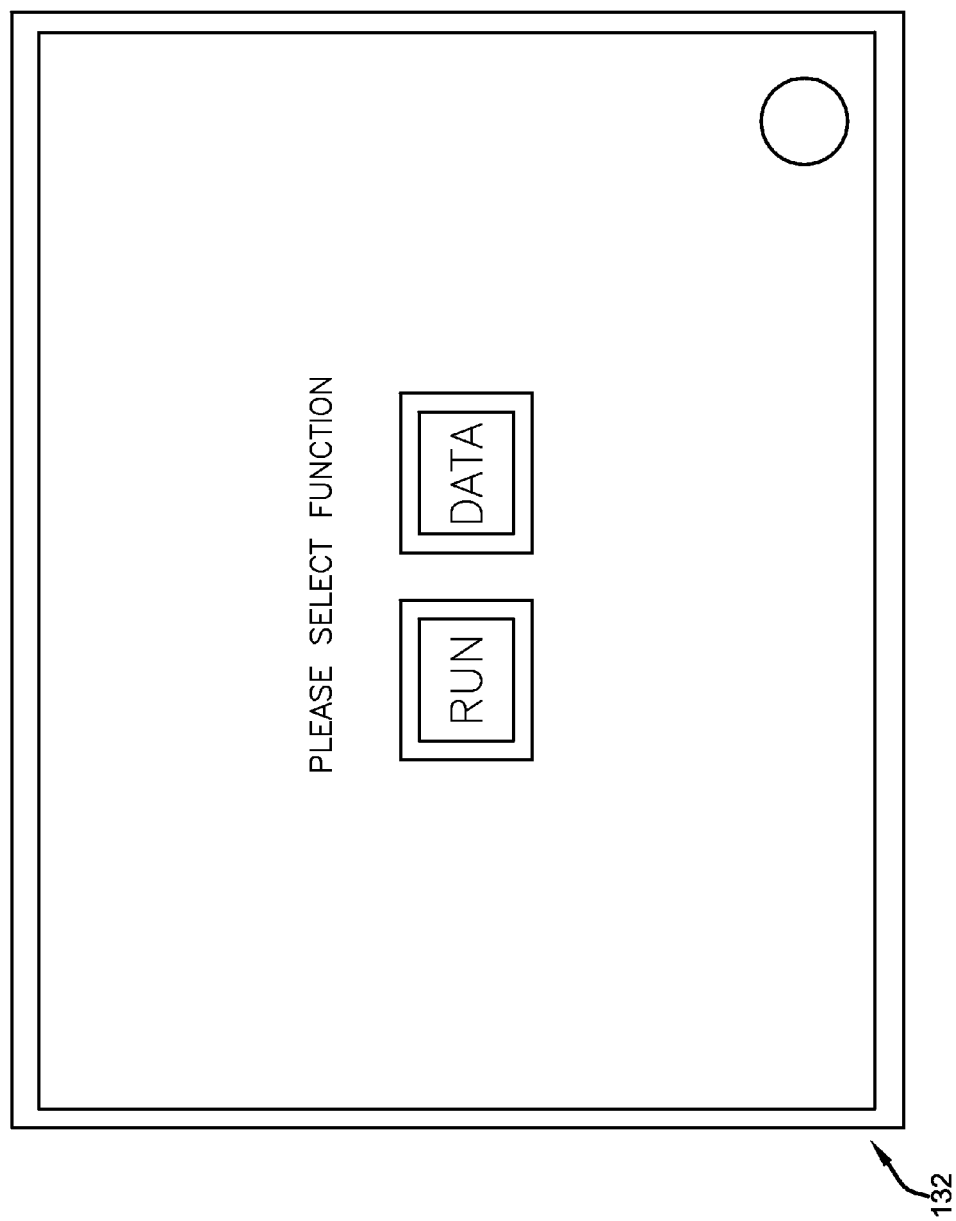
FIG. 6 is a view of still other embodiments of a control module.
Figure 7:
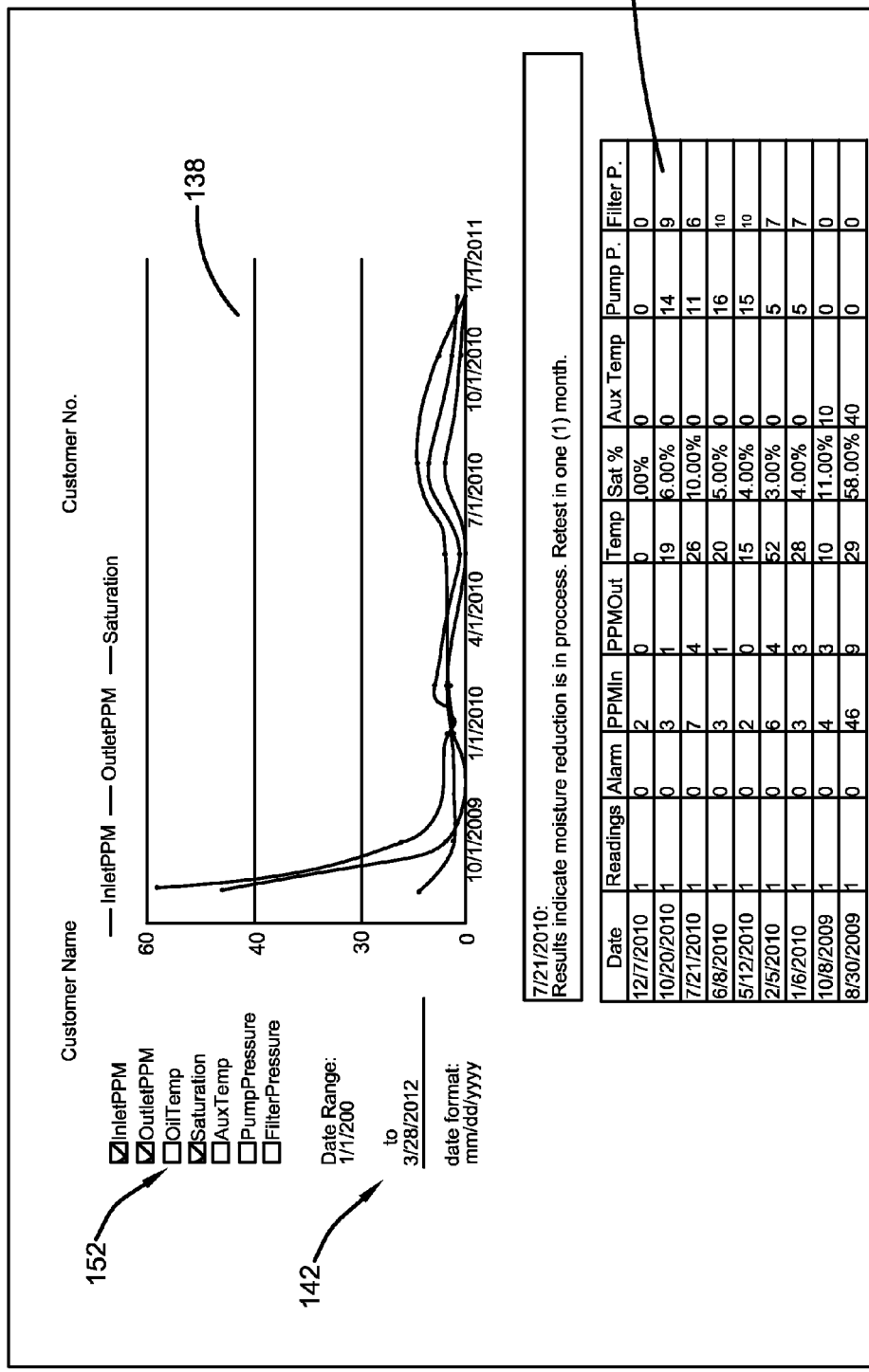
FIG. 7 is a view of some embodiments of a monitoring dashboard.

For the embodiment shown in FIG. 2, the control module 132 is mounted to the housing 100; specifically, mounted to an outer surface of one of the sidewalls. The control module 132 may comprise a touch screen, as shown. FIGS. 4-6 show several examples of the information that the control module 132 may provide access to. It should be understood, however, that these are examples only as the control module 132 may provide access and/or control to any information chosen with the sound judgment of a person of skill in the art. FIG. 5 illustrates how in another embodiment the control module 132 may provide information regarding: inlet (oil) moisture level PPM (parts per million of moisture in the transformer), inlet (oil) temperature (degrees Celsius), pressure (oil) PSI (pounds per square inch), and H2, (hydrogen gas) level PPM (parts per million). It also shows basic operation information including ID (identification) # (number), main, and run. FIG. 6 illustrates how in another embodiment the control module 132 may provide information regarding: high (oil) pressure, high (oil), off, start, stop, main and data. FIG. 7 illustrates how in another embodiment the control module 132 may provide information regarding: run and data. Some or all of the variables described may also be monitored to set off an alarm should the measured/determined value go above or below a predetermined value.

Figure 8:
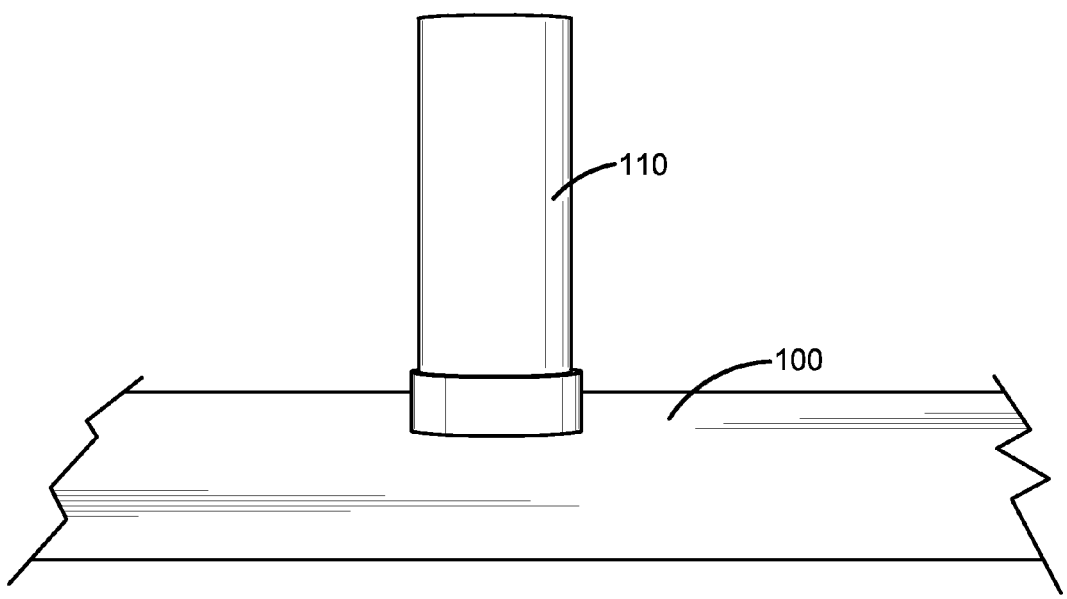
FIG. 8 is a view of a transmitter antenna mounted to the top of a housing.
Figure 9:
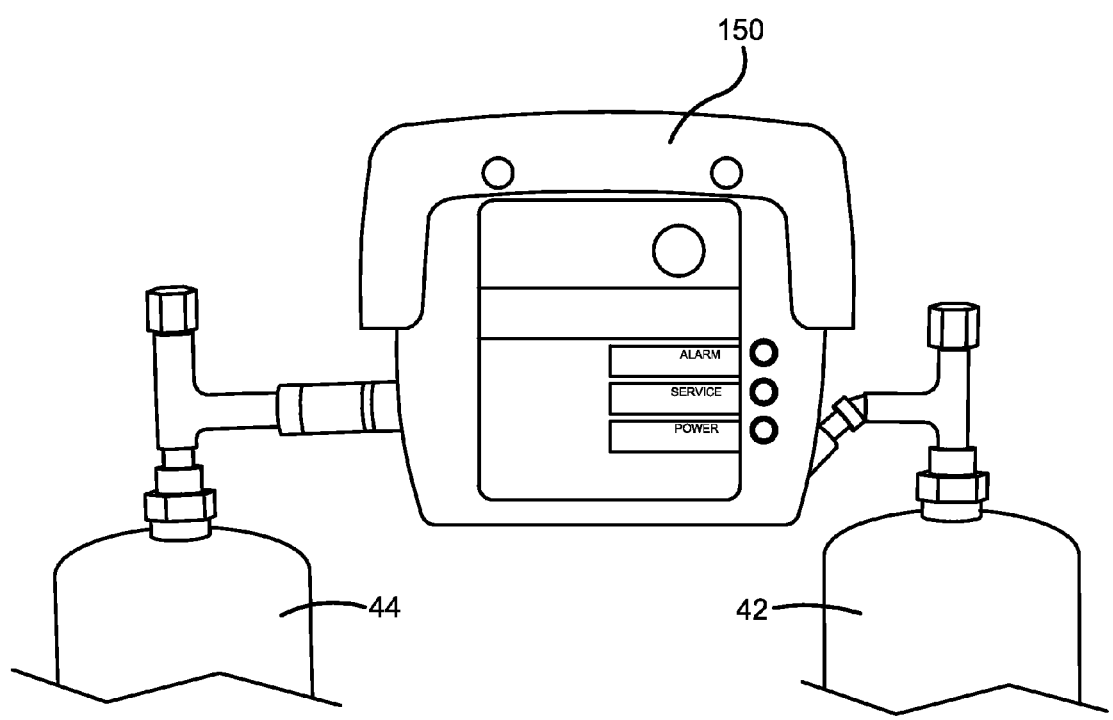
FIG. 9 is a front view of a hydrogen gas monitor.

With reference now to FIGS. 2 and 7-8, the control module 132 may be remote from remote from the transformer 10 and/or housing 100. In one embodiment, the control module 132 is provided on a computer monitor. The computer monitor may be located anywhere in the world chosen with the sound judgment of a person of skill in the art. Data may be transmitted wirelessly such as, for example, via cellular or Ethernet connection. The housing 100 may include a wireless antenna 110 for transmitting the data/information the various components generate and for receiving control signals.

FIG. 8 shows examples of the information that the monitoring dashboard 134 may provide access to. It should be understood, however, that these are examples only as the monitoring dashboard 134 may provide access and/or control to any information chosen with the sound judgment of a person of skill in the art. FIG. 8 shows a graph 138 with value of the variable indicated in the vertical axis ("Y-axis") and the date indicated in the horizontal axis ("X-axis"). The three variables shown are inlet (oil) moisture PPM (parts per million), outlet (oil) moisture PPM (parts per million), and percent saturation. FIG. 8 also shows a table 140 showing the same information that is shown on the graph 138. The monitoring dashboard 134 thus may be used to show the history of the various variables. As shown in portion 152 of FIG. 8, the graph 138 and table 140 may be adjusted to display additional (or in place of) information including Oil Temp (oil temperature), Aux Temp (auxiliary temperature), Pump Pressure, and Filter Pressure. The date range and format could also be adjusted as shown in portion 142. Some or all of the variables described may also be monitored to set off an alarm should the measured/determined value go above or below a predetermined value.

With reference now to all the FIGURES, the control and monitoring system 130 may include sensors, meters, temperature detectors, volt meters, and the like corresponding to the variables that are controlled and/or monitored. Thus, for example, a moisture monitor 144, a level alarm 146, and a hydrogen gas monitor 150 (see especially FIG. 10) may be incorporated into the control and monitoring system 130. Here is a typical list of statistics that the control and monitoring system 130 may keep:

Service:
1. Indications from a component of the machinery not properly functioning
2. Filter container pressure
3. Leak detection
4. Transformer Isolation
5. Alarm and Alert Conditions Fault Gas:
1. Hydrogen is standard, but other sensors are optional
2. Levels of gas
3. Rate of change of gas
4. Alarm levels based on level of gas Moisture:
1. PPM of water
2. Percent saturation
3. Temperature
4. Alarm levels based on saturation Oil Quality:
1. Monitor aging factors with oil sampling—posted to the monitoring dashboard
2. Tied to service on the Filter containers With reference again to all the FIGURES, in use a system for monitoring and treating transformer oil 30 having the desired components is located near the transformer 10 having the oil that is to be treated. The oil filtration system 40 is then connected to the transformer 10. In one embodiment, this is easily accomplished simply by connecting one end of the hoses 76, 76 to the housing 100 and the other ends to the transformer 10. Once the housing 100 and its components are properly connected to the transformer 10, the oil movement system 70 can be operated to move the transformer oil from the transformer 10, through the oil filtration system 40 and back to the transformer 10. This movement of the oil may be continuous and may occur while the transformer 10 is on-line. As the oil is moved through the oil filtration system 40, acids and moisture is removed from the oil as described above. The various sensors and meters are then used to monitor the desired characteristics of the oil. The control module 132 may be used to operate, receive and display the relevant data and/or control the system for monitoring and treating transformer oil 30. The monitoring dashboard 134 may also (or instead) be used to receive and display the relevant data and/or control the system for monitoring and treating transformer oil 30. In one embodiment, the monitoring dashboard 134 is monitored regularly. Should an adjustment become necessary, say for example an alarm or alert is activated at the monitoring dashboard 134, persons at the location of the transformer 10 can be notified to take whatever action may be necessary. Any of the information gathered or determined may be posted on an internet based data center. This data center may be properly protected so that only persons with access can review it and/or control the system for monitoring and treating transformer oil 30.

In some embodiment, the control module screens can be operated remotely and separate from the transformer dashboard data screens. In some embodiments, the system monitors itself for characteristic including: leak detection, high pressure and low pressure, It may automatically shut off when a leak is detected or if the pressure rises above a predetermined value, such as 40 PSI. If the system is used when the transformer is off-line, the pressure must remain low enough, since the system described does not have a heating device. If the oil gets too cold, the pressure will increase and once it hits the designated level the system will shut down.

Numerous embodiments have been described, hereinabove. It will be apparent to those skilled in the art that the above methods and apparatuses may incorporate changes and modifications without departing from the general scope of this invention. It is intended to include all such modifications and alterations insofar as they come within the scope of the appended claims or the equivalents thereof.

I claim:

1. A system for monitoring and treating transformer oil within an associated on-line electric transformer comprising:
   (A) an oil filtration system comprising:
      (1) a first filter container comprising a first filter medium that removes acids dissolved in the transformer oil from the transformer oil; and,
      (2) a second filter container comprising a second filter medium that removes moisture from the transformer oil;
   (B) an oil movement system that moves the transformer oil from the associated on-line transformer, through the transformer oil filtration system, and back into the associated on-line transformer; the oil movement system comprising a pump;
   (C) a housing located near the associated on-line electric transformer that houses the first and second filter containers and the pump; and,
   (D) a control and monitoring system that:
      (1) comprises a hydrogen sensor that: (a) is positioned within the housing; and,
      (b) senses the amount of hydrogen in the transformer oil;
      (2) comprises a moisture sensor that: (a) is positioned within the housing; and, (b) senses the amount of moisture and temperature of the transformer oil;
      (3) comprises a control module that: (a) is mounted to the housing; and, (b) receives and displays information from the hydrogen and moisture sensors;
      (4) comprises a monitoring dashboard remote from the housing that wirelessly receives and displays information from the hydrogen and moisture sensors;
      (5) determines parts per million (PPM) of moisture in the transformer oil;
      (6) determines the temperature of the transformer oil;
      (7) determines saturation of moisture in the in the transformer oil;
      (8) sets off an alarm or alert when certain predetermined operating conditions occur; and,
      (9) posts the information from the hydrogen and moisture sensors on an internet based data center.

2. The system for monitoring and treating transformer oil of claim 1 wherein the oil movement system moves the transformer oil through the first filter container before moving the transformer oil through the second filter container.

3. The system for monitoring and treating transformer oil of claim 1 wherein the first and second filter media are recyclable eliminating a need for disposal of the first and second filter media.

4. The system for monitoring and treating transformer oil of claim 3 wherein:
   the first filter medium primarily comprises granular alumina; and,
   the second filter medium primarily comprises alumina beads.

5. The system for monitoring and treating transformer oil of claim 4 wherein:
   the control module comprises a touch screen that is mounted to the housing.

6. The system for monitoring and treating transformer oil of claim 5 wherein the housing has an interior of about 24, cubic feet.

7. A system for monitoring and treating transformer oil within an associated on-line electric transformer comprising:
   (A) an oil filtration system comprising:
      (1) a first filter container comprising a first filter medium that removes acids dissolved in the transformer oil from the transformer oil; and,
      (2) a second filter container comprising a second filter medium that removes moisture from the transformer oil;
   (B) an oil movement system that moves the transformer oil from the associated on-line transformer, through the transformer oil filtration system, and back into the associated on-line transformer;
   (C) a housing located near the associated on-line electric transformer that houses the first and second filter containers; and,
   (D) a control and monitoring system comprising:
      (1) a hydrogen sensor that senses the amount of hydrogen in the transformer oil;
      (2) a moisture sensor that senses the amount of moisture and temperature of the transformer oil;
      (3) a control module juxtaposed to the housing that receives and displays information from the hydrogen and moisture sensors; and,
      (4) a monitoring dashboard remote from the housing that wirelessly receives and displays information from the hydrogen and moisture sensors.

8. The system for monitoring and treating transformer oil of claim 7 wherein the oil movement system moves the transformer oil through the first filter container before moving the transformer oil through the second filter container.

9. The system for monitoring and treating transformer oil of claim 7 wherein:
   the control module comprises a touch screen that is mounted to the housing;
   the oil movement system comprises a pump that is positioned within the housing;
   the hydrogen sensor is positioned within the housing; and,
   the moisture sensor is positioned within the housing.

10. The system for monitoring and treating transformer oil of claim 7 wherein the control and monitoring system:

determines parts per million (PPM) of moisture in the transformer oil;

determines the temperature of the transformer oil;

determines saturation of moisture in the in the transformer oil;

sets off an alarm when certain predetermined operating conditions occur.

11. The system for monitoring and treating transformer oil of claim 7 wherein the information from the hydrogen and moisture sensors is posted on an internet based data center.

12. The system for monitoring and treating transformer oil of claim 7 wherein the first and second filter media are recyclable eliminating a need for disposal of the first and second filter media.

13. The system for monitoring and treating transformer oil of claim 12 wherein:

the first filter medium primarily comprises granular alumina; and, the second filter medium primarily comprises alumina beads.

14. A method of monitoring and treating transformer oil within an associated on-line electric transformer comprising the steps of:

(A) providing a system for monitoring and treating the transformer oil within the associated on-line electric transformer that comprises: (1) an oil filtration system comprising: (a) a first filter container comprising a first filter medium; and, (b) a second filter container comprising a second filter medium; (2) an oil movement system; (3) a housing that houses the first and second filter containers; and, (4) a control and monitoring system comprising: (a) a hydrogen sensor; (b) a moisture sensor; (c) a control module juxtaposed to the housing; and, (d) a monitoring dashboard remote from the housing;

(B) locating the housing near the associated on-line electric transformer;

(C) connecting the oil filtration system to the associated on-line electric transformer;

(D) using the oil movement system to move the transformer oil from the associated on-line transformer and through the transformer oil filtration system;

(E) removing acids dissolved in the transformer oil from the transformer oil as the transformer oil is moved through the first filter container;

(F) removing moisture from the transformer oil as the transformer oil is moved through the second filter container;

(G) using the hydrogen sensor to sense the amount of hydrogen in the transformer oil;

(H) using the moisture sensor to sense the amount of moisture and the temperature of the transformer oil;

(I) using the control module to operate and to receive and display information from the hydrogen and moisture sensors;

(J) using the monitoring dashboard to wirelessly receive and display information from the hydrogen and moisture sensors; and, (K) using the oil movement system to move the transformer oil back into the associated on-line transformer;

wherein steps (A) through (K) slow the natural aging process of the associated on-line electric transformer.

15. The method of claim 14 wherein steps (D) and (K) are done continually.

16. The method of claim 14 wherein step (E) is done before step (F).

17. The method of claim 14 further comprising the step of:

recycling the first and second filter media as needed to eliminate a need for disposal of the first and second filter media.

18. The method of claim 14 further comprising the step of: using the control and monitoring system to:

determine parts per million (PPM) of moisture in the transformer oil;

determine the temperature of the transformer oil;

determine saturation of moisture in the in the transformer oil; and, set off an alarm when at least one of the following conditions occurs: (1) the PPM of moisture in the transformer oil is determined to be above a predetermined value; (2) the temperature of the transformer oil is determined to be above a predetermined value; and, (3) the saturation of moisture in the in the transformer oil is determined to be above a predetermined value.

19. The method of claim 14 further comprising the step of: posting the information from the hydrogen and moisture sensors on an internet based data center.

20. The method of claim 14 further comprising the step of: controlling the system for monitoring and treating the transformer oil via a remote cellular transmission.

\* \* \* \* \*